United States Patent [19]
Smith et al.

[11] Patent Number: 5,993,633
[45] Date of Patent: Nov. 30, 1999

[54] CAPILLARY ELECTROPHORESIS ELECTROSPRAY IONIZATION MASS SPECTROMETRY INTERFACE

[75] Inventors: Richard D. Smith, Richland, Wash.; Joanne C. Severs, Hayward, Calif.

[73] Assignee: Battelle Memorial Institute, Richland, Wash.

[21] Appl. No.: 08/904,419

[22] Filed: Jul. 31, 1997

[51] Int. Cl.[6] .................................................. G01N 27/26
[52] U.S. Cl. ........................ 204/601; 204/450; 250/288
[58] Field of Search ..................... 204/450, 603; 7/451, 452, 601; 436/173, 174; 250/288

[56] References Cited

PUBLICATIONS

Severs et al. ("A New High–perfromance Interface for Capillary Electrophoresis/Electrospray ionization Mass Spectrometry", Rapid Communications in MAss Spectrometry, vol. 10, 1175–1178, month unknown. 1996).

Lamoree et al. ("On–line coupling of micellar electrokinetic chromatography to electrospray mass spectrometry", Journal of Chromatography A, 712 (month unknown 1995) 219–2250 month unknown.

Lamoree et al. ("Use of heptakis92,6–di–o–methyl)B–cyclodextrin in on–line capillary zone electrophoresis–mass spectrometry for the chiral separation of ripivacaine", Journal of Chromathography A, 742 (month unknown 1996) 235–242).

Liquid Junction Coupling for Capillary Zone Electrophoresis/Ion Spray Mass Spectrometry, ED Lee, W Much, JD Henion, TR Covey, Biomedical and Environmental Mass Spectromety, vol. 18, 844–850 (1989) Month unknown.

*Primary Examiner*—Robert Warden
*Assistant Examiner*—Alex Noguerda
*Attorney, Agent, or Firm*—Paul W. Zimmerman

[57] ABSTRACT

The present invention is an interface between a capillary electrophoresis separation capillary end and an electrospray ionization mass spectrometry emitter capillary end, for transporting an anolyte sample from a capillary electrophoresis separation capillary to a electrospray ionization mass spectrometry emitter capillary. The interface of the present invention has: (a) a charge transfer fitting enclosing both of the capillary electrophoresis capillary end and the electrospray ionization mass spectrometry emitter capillary end; (b) a reservoir containing an electrolyte surrounding the charge transfer fitting; and (c) an electrode immersed into the electrolyte, the electrode closing a capillary electrophoresis circuit and providing charge transfer across the charge transfer fitting while avoiding substantial bulk fluid transfer across the charge transfer fitting. Advantages of the present invention have been demonstrated as effective in providing high sensitivity and efficient analyses.

9 Claims, 12 Drawing Sheets

CAPILLARY ELECTROPHORESIS ELECTROSPRAY IONIZATION MASS SPECTROMETRY INTERFACE

This invention was made with Government support under Contract DE-AC06 76RLO 1830 awarded by the U.S. Department of Energy. The Government has certain rights in the invention.

FIELD OF THE INVENTION

The present invention relates generally to an interface between a capillary electrophoresis (CE) separation capillary and an electrospray ionization (ESI) mass spectrometry (MS) emitter capillary.

BACKGROUND OF THE INVENTION

Interfacing between a CE to an ESI-MS is increasingly used in biomedical and biochemical applications with minute sample volumes and high-speed analyses. Several approaches for interfacing (i.e. establishing electrical contact at or near the end of the CE capillary) have been done.

In U.S. pat. No. Re. 34,757, 1994 (4,885,076, 1989), shows a CZE with a high voltage power supply in series with an EIS high voltage power supply spraying into an MS skimmer. Although high sensitivity and efficiency was achieved, disadvantages included (1) a dependence on the buffer system used, (2) ESI instability under some operating conditions and (3) the need to regularly replace the metal coating on the capillary tip.

In U.S. pat. No. 5,423,964, 1995 to Olivares et al., also spraying into a skimmer, a metal coating on the tip of the CE capillary made contact with a metal sheath capillary to which the CE terminus/ESI voltage was applied. In addition, a non-conductive capillary in combination with applying the EIS high voltage to a co-axial sheath flow was used. The sheath liquid, with a small electrolyte content, is infused to the ESI source through a sheath capillary surrounding the end of the separation capillary and terminating near the end of the separation capillary. The sheath liquid flowing at a few microliters per minute is added to the CE effluent as it elutes from the terminus of the CE capillary thereby providing the necessary electrical contact. The sheath-liquid interface has been widely employed, but not without shortcomings. The sheath-liquid composition must be carefully selected to avoid formation of moving ionic boundaries inside the capillary from migration of sheath-liquid counterions into the CE capillary. These ionic boundaries may cause variation in migration time and resolution. In addition, the sheath liquid incorporates impurities and other charge carrying species that can be ionized by the electrospray process and decrease overall sensitivity.

A sheathless design has been reported by SA Hofstadler, F D Swanek, J C Severs, A G Ewing and R D Smith, Rapid Commun. Mass Spectrom., "Analysis of Single Cells with Capillary Electrophoresis Electrospray Ionization Fourier Transform Ion Cyclotron Resonance Mass Spectrometry", S. A. Hofstadler, J. C. Severs, R. D. Smith, F. D. Swanek and A. G. Ewing, Rapid Commun. Mass Spectrom., 10, 919–922 (1996), wherein the capillary terminus was tapered and coated with gold. Fabrication of the gold-coated, tapered capillaries adds time and complexity to obtaining MS results. A flow-rate minimum limit of approximately 70 nL/min has been reported for the sheathless interface with improvements obtained if run at higher flow-rates (up to 250 nL/min), Bateman, K.; Thibault, P.; White, R. presented at the 44th ASMS Conference of the American Society for Mass Spectrometry and Allied Topics, Portland, Oreg., 1996.

The paper by E. D. Lee, W. Muck, J. D. Henion and T. R. Covey, Biomed. and Env. Mass Spectrom. 18, 844 (1989), discusses a liquid junction as an interface. Electrical contact is established through a liquid reservoir surrounding the junction of the separation capillary and a "transfer" capillary. A gap between the two capillaries is adjusted to about 10–20 micrometer permitting sufficient make-up liquid from the reservoir to be drawn into the transfer capillary and avoiding anolyte loss. Of course, elecrophoretic separation is terminated at the discontinuity of the gap. The flow of make-up liquid into the "transfer" capillary is induced by a pressure difference (generally arising due to some combination of differences in height of the two ends of the capillary and the venturi effect of the nebulizing gas at the capillary tip). One of the disadvantages of the liquid junction interface is the difficulty in establishing a reproducible spacing of the capillary segments, and the fact that both the anolyte transfer efficiency and the flow rate of added liquid from the reservoir are critically dependent on this spacing.

A disadvantage of both the sheath-flow and liquid junction interfaces is the need for electrolyte added to the ESI source (emitter) to maintain the electrical circuit. This added electrolyte often decreases biological or chemical molecule detection sensitivity. And, as stated previously, disadvantages of the sheathless gold-coated, tapered capillary include the complexity of assembly, and a special terminus on the CE capillary is required. Accordingly, there is a need for CE-ESI-MS interface that is simple to assemble and operate, specifically neither requiring gold plating nor requiring added electrolyte (buffer), but permitting operating at low flow rates for a wide range of liquid compositions.

SUMMARY OF THE INVENTION

The present invention is an interface between a capillary electrophoresis separation capillary end and an electrospray ionization mass spectrometry emitter capillary end, for transporting an anolyte sample from a capillary electrophoresis separation capillary to a electrospray ionization mass spectrometry emitter capillary. The interface of the present invention has:
 (a) a charge transfer fitting enclosing both of the capillary electrophoresis capillary end and the electrospray ionization mass spectrometry emitter capillary end;
 (b) a reservoir containing an electrolyte surrounding the charge transfer fitting; and
 (c) an electrode immersed into the electrolyte, the electrode closing a capillary electrophoresis circuit and providing charge transfer across the charge transfer fitting while avoiding substantial bulk fluid transfer across the charge transfer fitting.

As used herein, the term "charge transfer fitting" is used to describe an element that mechanically holds two capillary ends together permitting flow from one capillary end into the other longitudinally through the charge transfer fitting while at the same time permitting electrical charge to pass transversely through the fitting while avoiding bulk flow transversely through the charge transfer fitting.

Advantages of the present invention have been demonstrated as effective in providing high sensitivity and efficient analyses. The present invention interface may operate with sharply tapered emitters and with or without the addition of any 'make-up' liquids, thereby increasing sensitivity and eliminating ionic boundary formation under normal operation. The ability to operate at lower flowrates relative to the 'sheathless' interface has also been demonstrated, providing the capability for operation on-line with a wider range of CE conditions for separation optimization.

The present invention also avoids the need to coat the electrophoretic capillary terminus with a metal contact, greatly reducing capillary preparation time and increasing flexibility in the use of different capillaries. The placement (e.g., aligning and gluing) of the two capillaries inside the micro-dialysis tube is simple (easily or readily accomplished), reproducible and inexpensive. Additionally, the components of separation capillaries and electrospray emitters may now be optimized independently, with the small etched emitters readily produced in batches. The tips, detached from the CE voltage via a junction, also last longer than their conductive gold-tipped counterparts, and are less prone to problems arising from electrical breakdown. Acidification of the CE effluent has also been demonstrated for providing post-separation solution changes.

As well as providing improved sensitivity in the higher m/z range relative to the 'sheathless' interface, the interface of the present invention maintains effective ESI interface operation at lower CE flow-rates, and therefore operates with a broader range of CE separation conditions.

It is an object of the present invention to provide a reliable, flexible, and rugged CE-ESI-MS interface.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
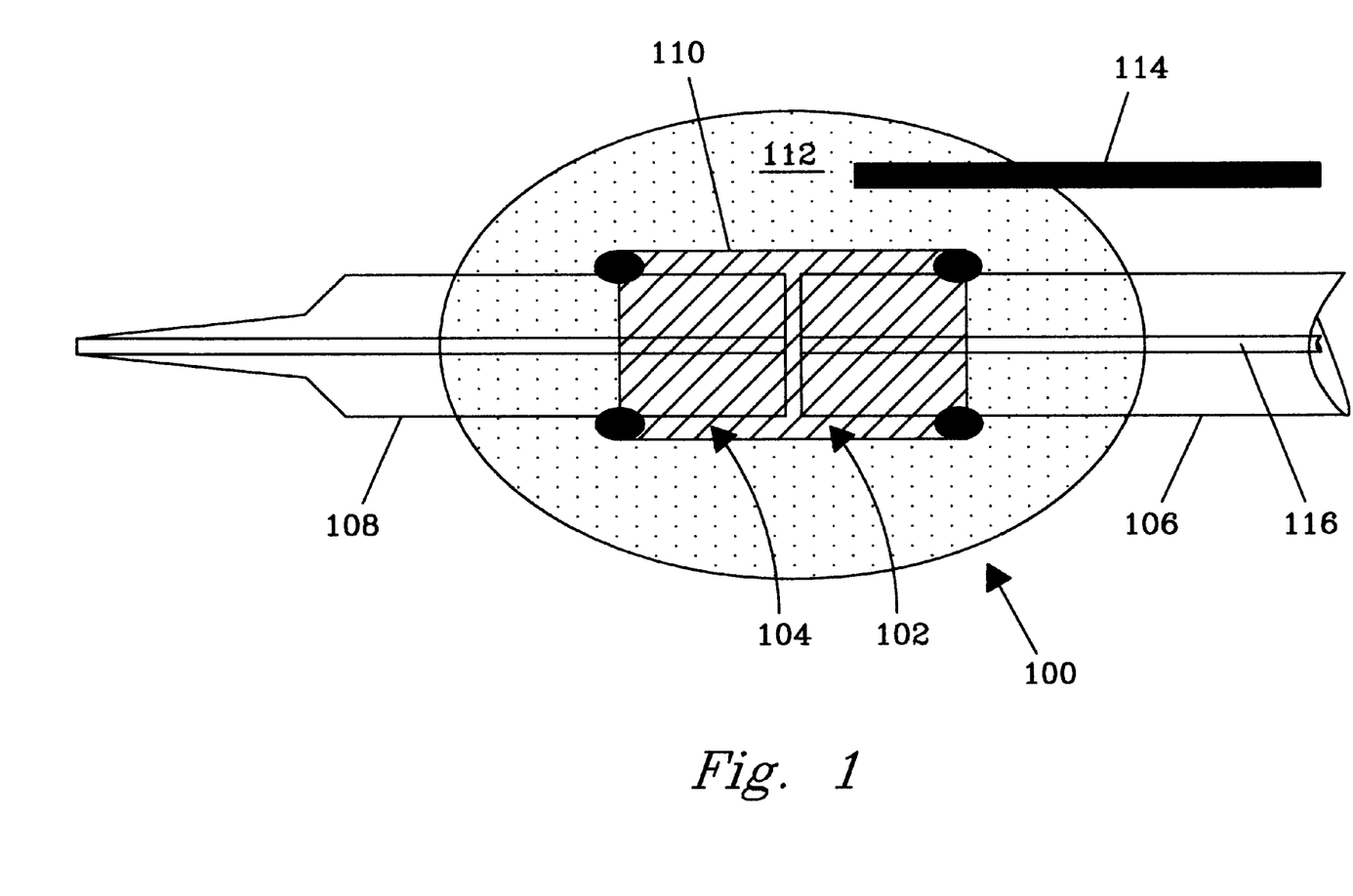
FIG. 1 is a cross section of the interface of the present invention.

Referring to FIG. 1, the present invention is an interface 100 between a capillary electrophoresis separation capillary end 102 and an electrospray ionization mass spectrometry emitter capillary end 104, for transporting an anolyte sample from a capillary electrophoresis separation capillary 106 to a electrospray ionization mass spectrometry emitter capillary 108. The anolyte sample is made up of a background electrolyte and a biological or chemical molecule. Background electrolyte may be any electrolyte including but not limited to acetic acid, ammonium acetate, ammonium carbonate, and combinations thereof. Biological molecules amenable to analysis include but are not limited to carbohydrates, glycoproteins, peptides, and proteins, nucleotides, ologonucleotides, and DNA-protein complexes, DNA segment, synthetic polymers biopolymers and combinations thereof.

The interface 100 has a charge transfer fitting 110 enclosing both of the capillary electrophoresis capillary end 102 and the electrospray ionization mass spectrometry emitter capillary end 104. The interface 100 further includes a reservoir (not shown) containing an electrolyte 112 surrounding the charge transfer fitting 110, and an electrode 114 immersed into the electrolyte 112, the electrode 114 closing a capillary electrophoresis circuit (not shown) and providing charge transfer transversely across the charge transfer fitting from the electrode 114 through the electrolyte 112 and through the charge transfer fitting 110 to the anolyte sample 116. The charge transfer fitting 110 may permit transverse charge transfer in part or in whole over its surface area. The electrolyte 112 may be any electrolyte having a conductivity appropriate for CE including but not limited to acetic acid, ammonium acetate, ammonium carbonate, and combinations thereof. Preferred are more volatile electrolytes, e.g. ammonium acetate to obtain enhanced performance.

The electrospray ionization mass spectrometry emitter capillary 108 is preferably less than about 10 cm in length and more preferably less than 3 cm in length. Emitters 108 with lengths greater than 3 cm were found to be less reliable in providing a constant flow to the ESI source. Shortening the length to 2 cm improved performance.

The charge transfer fitting 110 may be any fitting permitting charge transfer from the electrolyte 112 to the anolyte sample 116. In a preferred embodiment, the charge transfer fitting 110 is microdialysis tubing. It is further preferred that the electrolyte 112 is substantially electrochemically similar to the anolyte sample 116 in order to avoid substantial bulk fluid transfer across the charge transfer fitting 110. Electrochemically similar means that the anolyte sample 116 and the electrolyte 112 do not substantially transfer ions or bulk fluid under an electrical potential. Substantial ion transfer or bulk fluid transfer is sufficient to affect MS analysis results.

The reservoir may be closed or open, or of any material, but an open reservoir is preferred, rather than an enclosed/limited reservoir, and plastic is preferred rather than metal, to avoid the production of air bubbles in the electrolyte circuit.

The high voltage power supply (HVPS) (not shown) to the ESI interface is connected to the electrode 114, preferably copper wire. A common ground connection is also formed between the CE system, the outer casing of the ESI HVPS lead and the mass spectrometer. Because the mass spectrometer does not act as a current sink, previous attempts at constructing CE-ESI-MS interfaces have occasionally resulted in damaging discharges to the ESI system when the high voltage was applied and the gold contact was disturbed. In the present invention, the potential across the CE circuit terminates in a stable electrical contact prior to the ESI emitter, thereby avoiding the damaging discharges.

Another important feature of this interface 100 is that it does not distort or alter the CE separation. Under routine operating conditions the electrolyte outside the dialysis membrane (i.e., in the pipette tip) was the same as the CE background electrolyte in the anolyte sample, so there was no net ion transfer across the membrane, and no resulting ionic boundaries propagated into the separation capillary. However, the effect of purposefully changing the electrolyte in the reservoir, to change the solution conditions post-run, can also be exploited based upon this interface. The ability to acidify anolytes after a separation under neutral conditions, for example for the study of non-covalent interactions or capillary isoelectric focusing, is an attractive feature.

Example 1

An experiment was conducted to demonstrate the present invention.

Reagents and Materials. Deionized distilled water from a Nanopure II water system (Barnstead, Dubuque, Iowa) was used to prepare the electrolyte 112 surrounding the charge transfer fitting 110 and anolyte sample 116. Ammonium acetate was prepared from ammonium hydroxide and glacial acetic acid (Sigma, St. Louis, Mo.), and adjusted to the desired pH.

Fused silica capillaries of dimensions 192 $\mu$m o.d.$\times$30 $\mu$m i.d.$\times$70 cm, obtained from Polymicro Technologies Inc. (Phoenix, Ariz.), were employed for the capillary electrophoresis separation capillary 106 and the electrospray ionization mass spectrometry emitter capillary 108. The polyimide coating was removed from the last 2 cm of short lengths of silica capillary, and these portions were then etched in 40% hydrofluoric acid (Aldrich, Milwaukee, Wis.) for approximately 30 minutes. The resulting capillary was trimmed to produce a sharp emitter.

The charge transfer fitting 110 was a 250 $\mu$m i.d. polysulphone dialysis tubing (nominal molecular-weight cutoff of 10,000) obtained from A/G Technology Corporation (Needham, Mass.).

The capillary electrophoresis separation capillary 106 and the 2 cm long ESI mass spectrometer emitter capillary 108 were butted together inside a 1.5 cm length of the charge transfer fitting 110 and epoxy (not shown) was then applied around the outside of the charge transfer fitting/capillary boundaries forming the interface 100. After the epoxy had dried the interface 100 was inserted through a 250 $\mu$L eppendorf pipette tip (reservoir) containing the electrolyte 112. These plastic tips successfully hold liquid (electrolyte) even when positioned horizontally. The pipette tip was connected to an x-y-z rotating insulating stand, and a copper wire (electrode 114), attached to the stand, was extended into the electrolyte 112.

Instrumentation. A, Crystal 310 CE system (ATI Unicam, Madison, Wis.) was interfaced to a Finnigan TSQ 7000 triple quadrupole mass spectrometer equipped with an electrospray ionization interface (Finnigan MAT, San Jose, Calif.), employing a micro-spray ionization source as shown and described in D. C. Gale and R. D. Smith, *Rapid Commun. Mass Spectrom.*, 7, 1017, hereby incorporated by reference.

The spectrometer was tuned and calibrated using an acidic solution of myoglobin and FMAF infused at 0.3 $\mu$l/min. to the micro-spray source. The electron multiplier was set to 1.3 kV and the conversion dynode to –15 kV. The heated desolvation capillary in the ESI source was held at 150° C. CE-MS spectra were acquired either full-scan (2 seconds per scan) or using selected-ion-monitoring with a total step-cycle time of 1 second.

The high voltage power supply (HVPS) to the ESI interface was connected to the copper wire and a common ground connection was also formed between the CE system, the outer casing of the ESI HVPS lead and the TSQ 7000 system.

An amount of the electrolyte 112 was pressurized through the separation capillary for a few minutes to condition the walls and the ESI voltage was applied and optimized at 1.6 kV before injecting the anolyte sample and applying the separation voltage.

Anolyte sample was bovine carbonic anhydrase II purchased from Sigma, and the small benzenesulphonamide library was provided by Prof. G. Whitesides, Harvard, (C. Liu, Q. Wu, A. C. Harms and R. D. Smith, *Anal Chem.*, (submitted)).

When the separation voltage was applied with the present design a completed circuit was immediately observed, as characterized by a rise in the ESI current observed on the TSQ monitor. At no time were disruptions in the CE circuit ever observed; i.e., the electrical connection across the membrane was reliably maintained. Occasionally the ESI process faltered due to a blockage of the tip. This was effectively remedied by filtering the buffers and electrolyte solutions and could usually be reversed by placing the tip in water for a few minutes. Unlike the liquid-junction interface, there was no need to optimize a gap between the two capillaries; the capillaries were simply pushed together as no inlet flow of liquid or electrolyte through the junction was necessary.

Figure 2:
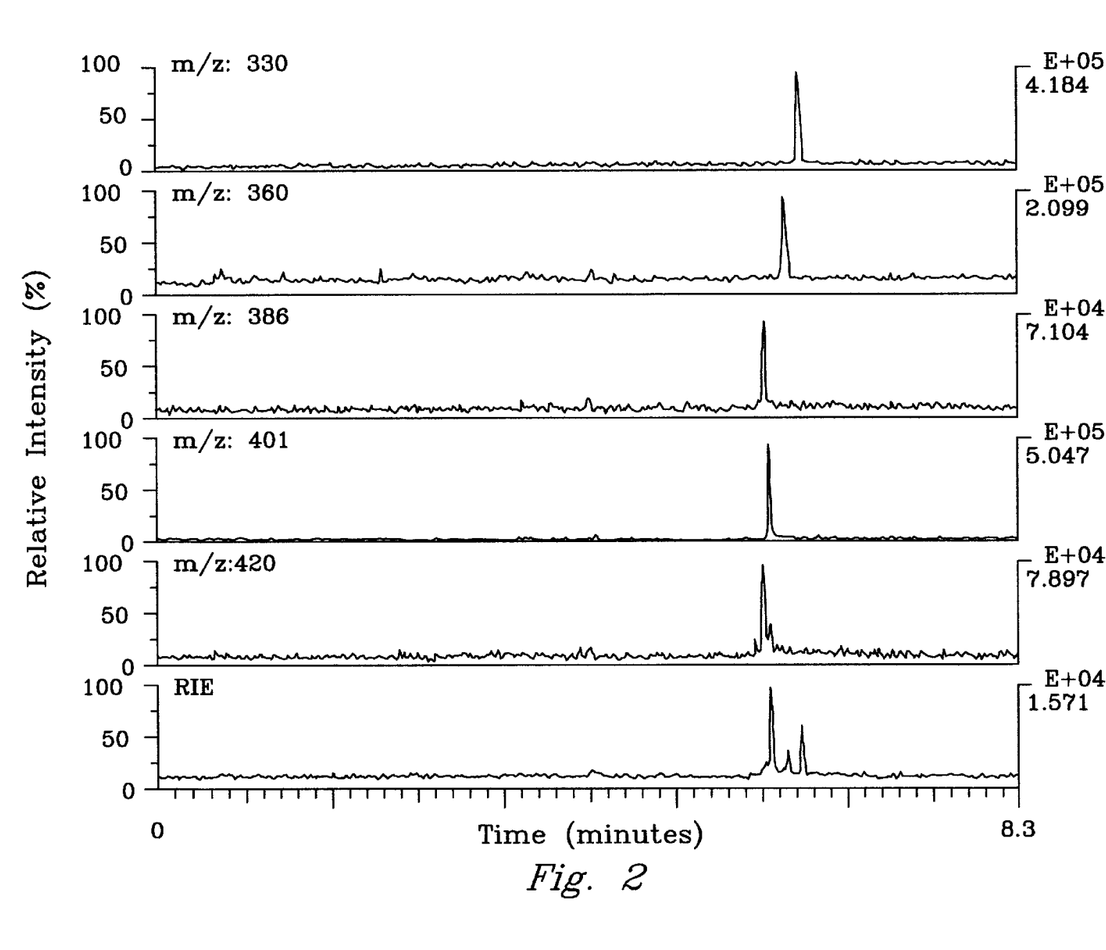
FIG. 2 is a set of mass electropherograms for a CE-ESI-MS separation of a set of benzenesulphonamides (MWs.: 329, 359, 385, 400, 419), employing a micro-dialysis membrane tubing junction. Background electrolyte=20 mM $NH_4OAc$ (pH 8.3), 30 kV, selected-ion-monitoring.

The separation and detection of some small benzenesulphonamides with different amino acid tails, illustrated in FIG. 2, demonstrates clearly that this new interface can provide high efficiency separations. The CE peaks correspond to up to 350,000 theoretical plates. This analysis, conducted using a pH 8.5 ammonium acetate solution, demonstrates the generally obtainable low femtomole to high attomole level sensitivity, (a sample volume of 25 nL having 0.25 $\mu$g/mL concentrations initially being injected). Under acidic conditions even higher sensitivities were achieved. It is important to note that at no time, even under the low electroosmotic flow conditions using a pH 4.5 ammonium acetate solution, was the use of a pressure gradient across the separation capillary or across the membrane necessary to maintain the electric circuit and a stable electrospray. Only species from the CE separation were observed to be introduced to the electrospray source.

The electrospray process was also maintained even prior to the application of the separation voltage when an extremely sharp tip was employed. Because the etched emitters did not have to be exposed to refluxing and coating procedures, some extremely fine/sharp capillary tips were be employed. Even under infusion conditions it was seen that these finer emitters provided much more stable electrospray signals extending much higher in the m/z range, than obtained in our previous experience with gold-coated emitters. This improved sensitivity and also facilitated identification of proteins.

Example 2

An experiment was conducted wherein the anolyte sample was electrochemically dis-similar to the electrolyte. Chemicals and instrumentation were as in Example 1.

Bovine carbonic anhydrase II (BCA II) was injected from an initial concentration of 2 mg/mL in water, run with a background electrolyte of 20 mM ammonium acetate (pH 8.5) as an anolyte sample. Electrolyte varied from identical to the background electrolyte, to 3% acetic acid.

Figure 3A:
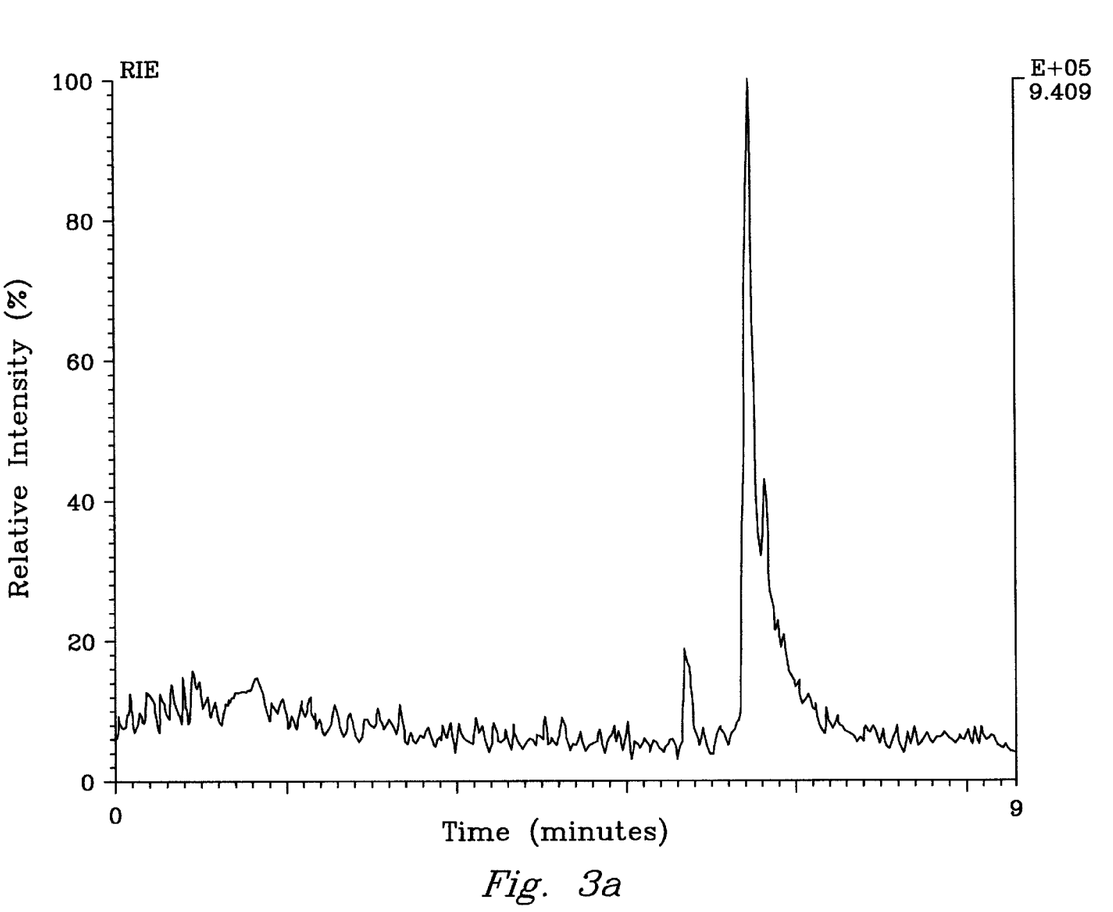
FIG. 3a is a reconstructed ion electropherogram from a CE-ESI-MS full scan analysis (m/z 1700–3300) of BCA II.
Figure 3B:
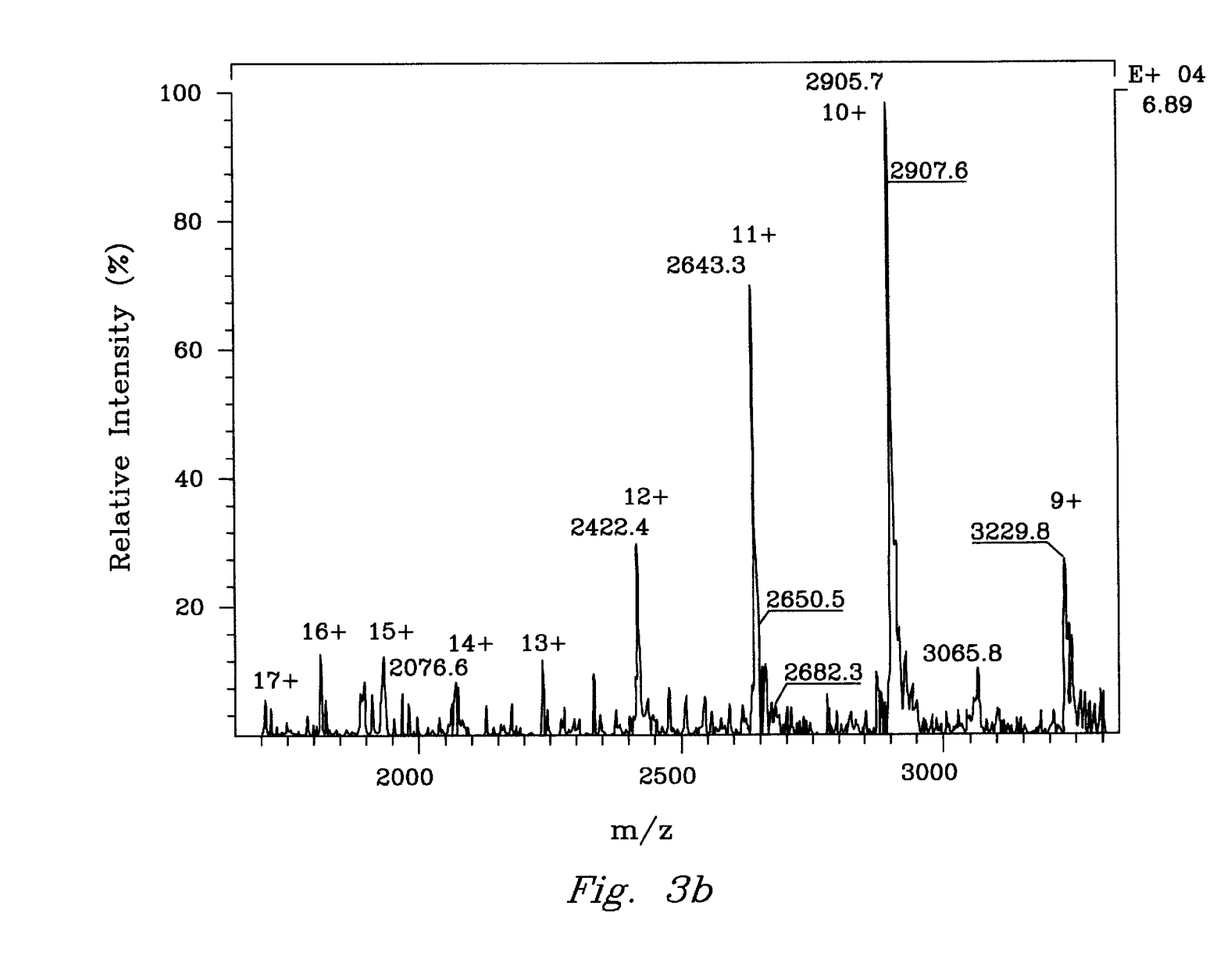
FIG. 3b is a mass spectrum of BCA II when junction electrolyte=background electrolyte=20 mM $NH_4OAc$ (pH 8.3).
Figure 3C:
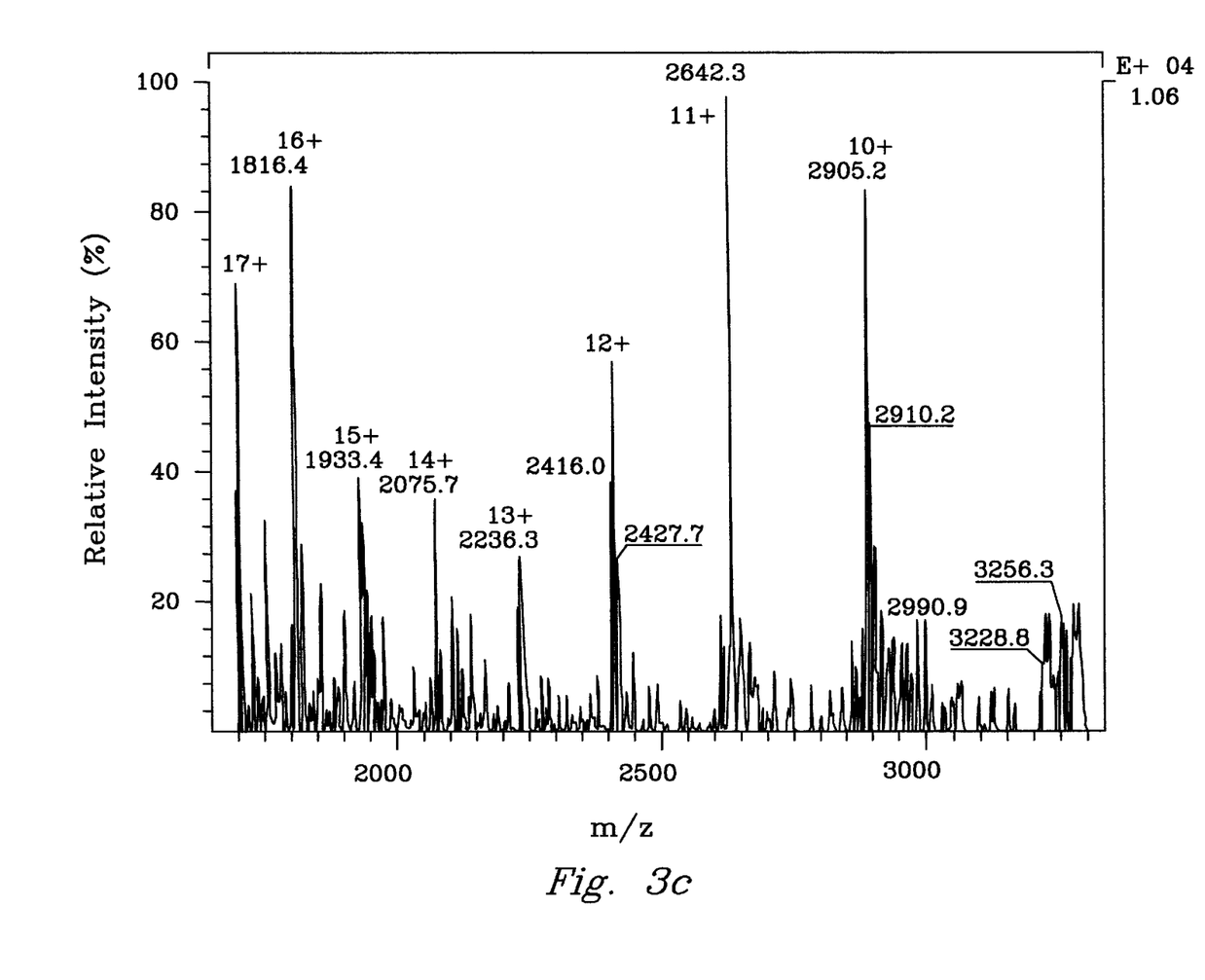
FIG. 3c is a mass spectrum of BCA II when junction electrolyte=3% acetic acid.

A CE-MS analysis (FIG. 3b) shows the mass spectrum obtained from under the major peak in FIG. 3a when the electrolyte in the reservoir was the same as the background electrolyte. FIG. 3c shows the resulting spectrum, in which a charge-state distribution shift can be observed, when the reservoir was changed to 3% acetic acid. Use of the 3% acetic acid resulted in a three minute delay in migration time, demonstrating an ionic boundary effect. This experiment clearly demonstrates the potential for manipulation of the external reservoir composition to manipulate both the separation and the ESI process.

Example 3

Additional experiments were conducted to demonstrate CE-ESI-MS for various anolyte samples in comparison to standard sheath flow methods. The reagents, materials and instrumentation were as in Example 1.

The separation and emitter capillaries were precoated internally with aminopropyltrimethoxysilane (Aldrich, Milwaukee, Wis.) to avoid analyte interaction with the charged capillary walls, when separating protein mixtures. In cases where elimination of the electroosmotic flow (EOF) through the capillaries was also desired, the capillaries were precoated externally with methacryloxypropyltrimethoxysilane (Aldrich) and then polyacrylamide (BRL Life Technologies, Gaithersburg, Md.).

Standard proteins and peptides were purchased from Sigma, and the small benzenesulphonamide library (Gao, J.; Cheng, X.; Chen, R.; Sigal, G. B.; Bruce, J. E.; Schwartz, B. L.; Hofstadler, S. A.; Anderson, G. A.; Smith, R. D.; Whitesides, G. M. *J. Med. Chem.*, 1996, 39, 1949–1955) and bovine carbonic anhydrase II (BCA II) charge ladder (Gao, J.; Gomez, F. A.; Haerter, R.; Whitesides, G. M. *Proc. Natl. Acad. Sci. USA* 1994, 91, 12027–12030) were provided by the laboratory of Prof. G. Whitesides, Harvard.

The micro-spray ionization source of Example 1 was used when using the interface 100 of the present invention and the standard Finnigan source when using a coaxial sheath flow system. The sheath flow, composed of 75:24:1 isopropanol:water:acetic acid, was infused via a Harvard syringe pump at a flow rate of 1 $\mu$L/min. The spectrometer was tuned and calibrated using an acidic solution of myoglobin and FMAF infused at 0.3 $\mu$l/min. through the micro-spray source. The electron multiplier was set to 1.3 kV and the conversion dynode to −15 kV. The heated desolvation capillary in the ESI source was held at 160° C. CE-MS spectra were acquired either full-scan (1 or 2 seconds per scan) or using selected-ion-monitoring with a total step-cycle time of 1 second.

For these tests, the flow-rate at the ESI emitter with the micro-dialysis junction interface was nearly the same as the flow-rate through the CE capillary (which is generally in the range of nL/min), demonstrating or confirming no significant mass transfer through the dialysis membrane, only ionic transfer. Moreover, the electrolyte in the reservoir was the same as the background electrolyte in the anolyte sample resulting in no net electrolyte addition, no anolyte ion dilution and no production of ionic boundaries.

Three parameters of primary importance for the performance of a CE-MS interface were analyzed. These are: (1) sensitivity, (2) separation efficiency, and (3) reliability or ruggedness of the interface.

Figure 4A:
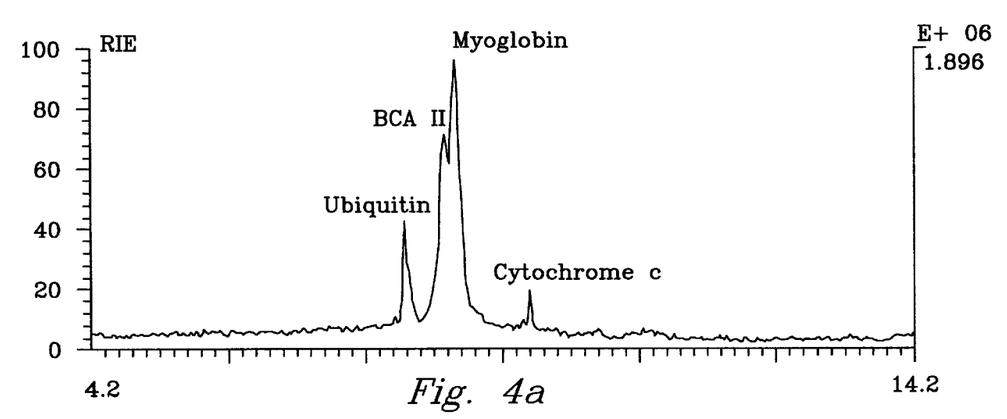
FIG. 4a is a protein mixture mass electropherogram obtained with a micro-dialysis junction (charge transfer fitting) with separation conditions of 30 micrometer ID×1.1 m APS coated capillary, 10 mM HOAc, 30 kV, m/z 1000–2600 in 2 sec.
Figure 4B:
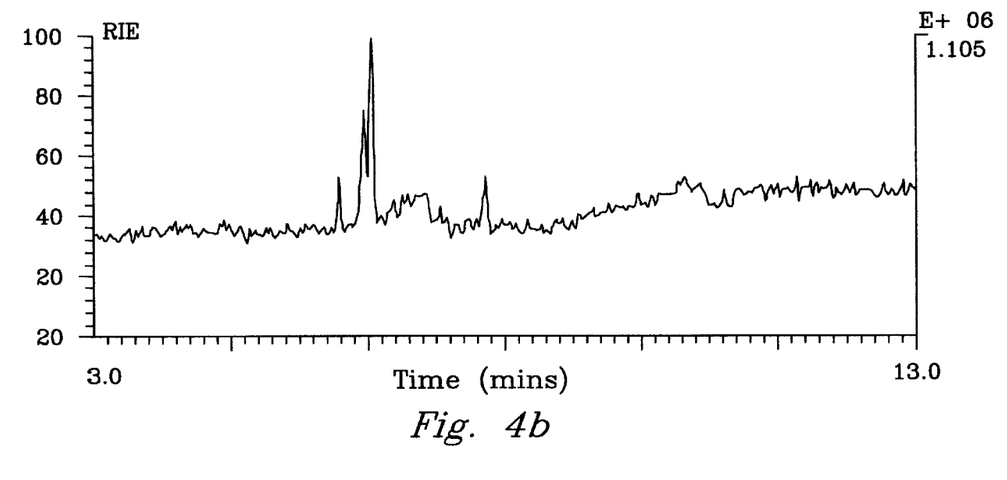
FIG. 4b is a protein mixture mass electropherogram obtained with a coaxial sheath-flow junction (75:24:1 $IPA:H_2O:HOAc$ at 1 microliter per minute) with separation conditions of 30 micrometer ID×1.1 m APS coated capillary, 10 mM HOAc, 30 kV, m/z 1000–2600 in 2 sec.

Sensitivity: FIGS. 4a and 4b demonstrates the surprising gain in sensitivity achieved employing the interface 100 (micro-dialysis junction) (FIG. 4a) for separation of a 10 $\mu$M protein mixture relative to that achieved employing the sheath-flow interface (FIG. 4b). Care was taken to ensure that equivalent separation parameters were employed in both cases, capillaries were conditioned identically and the same sample volumes were injected. For this comparison, in which the analyzer was scanning m/z 1000–2600 at 2 sec/scan, the sheath-flow was optimized and minimized to 1 $\mu$L/min (2–5 $\mu$L/min sheath-flows are generally reported). An optimized spray voltage of 3.7 kV was applied for ionization. The detection limit for the proteins under these full-scan conditions was approximately 10 $\mu$M when employing the sheath-flow system, but the biological or chemical molecules could still be detected when diluted 10-fold employing the micro-dialysis junction. Our studies to date indicate that approximately an order of magnitude improvement in detection limits was achieved.

Figure 5A:
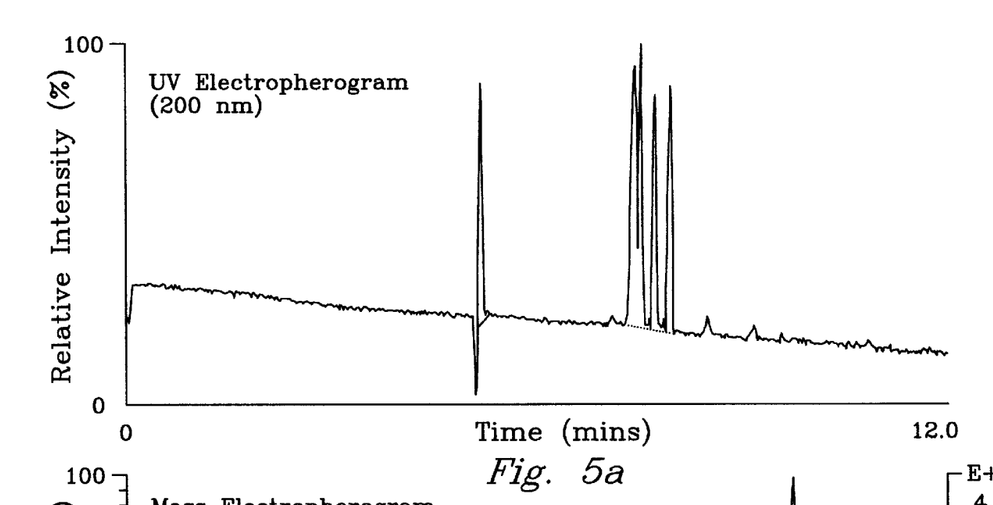
FIG. 5a is a mass electropherogram of benzenesulphonamides with a UV detection at 200 nm.
Figure 5B:
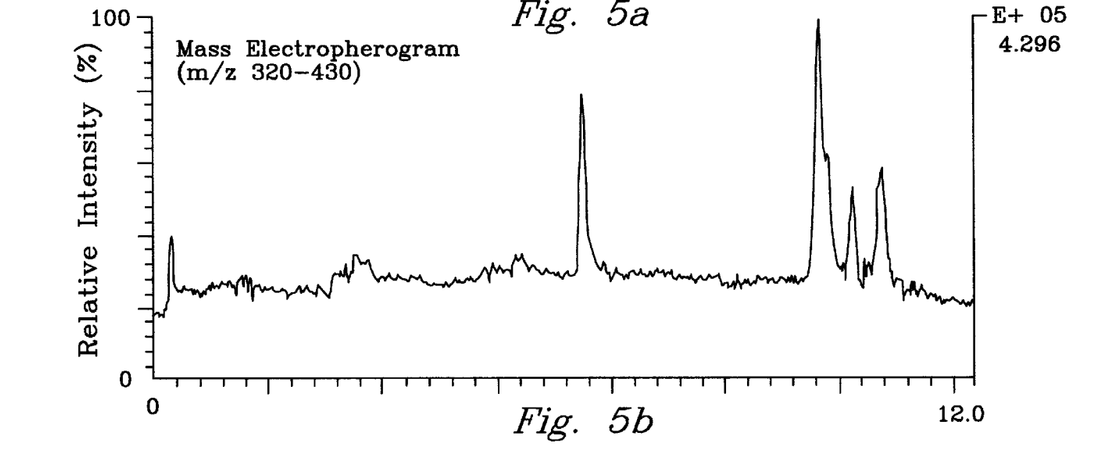
FIG. 5b is a mass electropherogram of benzenesulphonamides with ESI-MS detection over m/z 320–430 with a charge transfer fitting.

Separation Efficiency: FIGS. 5a and 5b shows a comparison of CE with on-capillary UV detection at 200 nm (FIG. 5a) and CE-ESI-MS employing the micro-dialysis interface (FIG. 5b) for a separation of several benzenesulphonamides. As can be seen, there is only a small loss in separation efficiency (<20%) and comparable sensitivity (full scan) is obtained. The specificity of mass spectral detection, however, means that any small loss of separation efficiency is generally unimportant. Although there is a slight efficiency loss relative to on-line UV detection, it should also be noted that efficiency retention is generally comparable to other mass spectral interfaces, as demonstrated in FIG. 4b for the sheath-flow interface.

Figures 6A, 6B:
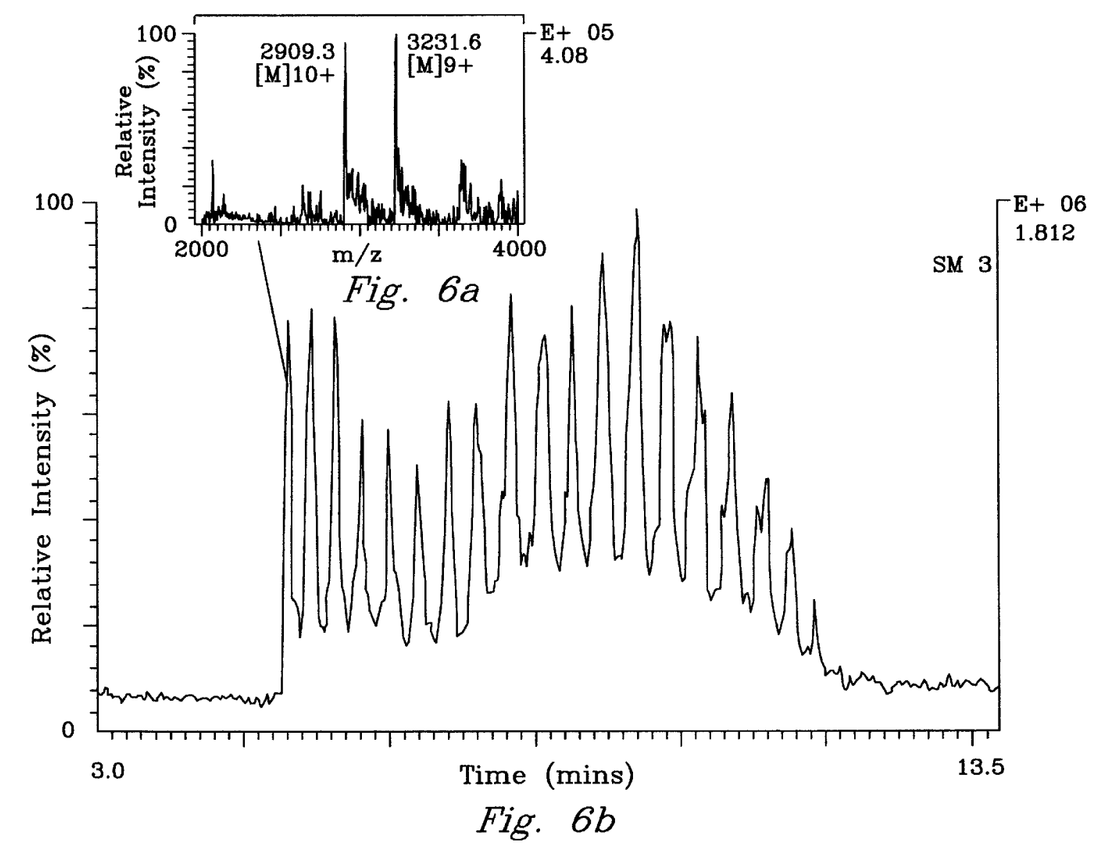
FIG. 6a is a mass spectrum of a charge ladder of bovine carbonic anhydrase II sample 15 mg/mL total protein with separation conditions of 30 kV for 3 min, reduced to 15 kV for remainder of run, 10 mM $NH_4OAc$ (pH 9), scanning m/z 2900–3390 at 1 sec/scan.
FIG. 6b is a mass electropherogram of a charge ladder of bovine carbonic anhydrase II sample 15 mg/mL total protein with separation conditions of 30 kV for 3 min, reduced to 15 kV for remainder of run, 10 mM $NH_4OAc$ (pH 9), scanning m/z 2900–3390 at 1 sec/scan.

FIGS. 6a and 6b shows a separation of a charge ladder of bovine carbonic anhydrase II. Each peak in this separation is due to an extra conversion of a positively-charged Lys $\epsilon$—$NH_3^+$ group on the protein surface to a neutral N-acyl derivative; the mixture is a set of protein derivatives differing in charge in solution by integral units. The CE separation due to the charge on the protein derivatives was maintained through the interface. Additionally, the ability to spray from a purely aqueous solution, without post-run addition of a sheath-flow, allowed the mass spectral analysis of native proteins at neutral pH conditions. The gold-coated 'sheathless' interface would also be expected to provide comparable performance, however, we found that some gold-coated tips, which are more difficult to make as sharply tapered as the tips now being employed (due to their need to withstand refluxing and coating procedures), did not provide useful mass spectra in the higher m/z range. In contrast, this experiment demonstrates that useful data can be readily obtained across the m/z range 1000–4000 using the micro-dialysis junction of the present invention under aqueous conditions.

Reliability: A stable electrical circuit has been immediately achieved with each junction so far constructed. For emitter capillaries limited to lengths of <2 cm, the reliability of this interface is significantly improved compared to other interfaces. As there is no potential difference across the emitter capillary, liquid flow through this short capillary section depends upon the EOF generated in the separation capillary, the pressure applied by the separation capillary eluant and any flow induced by the electrospray process. These parameters appear to not provide a sufficient flow through an emitter of length greater than 2 cm. Blockage of the 30 $\mu$m i.d. emitter tips is rare and can be further minimized by filtering electrolytes and storing tips in distilled water. (The tips can often be restored by careful trimming with a capillary cutter, if necessary.) Smaller diameter tips were investigated but were found to block too readily for routine utility.

Figure 7A:
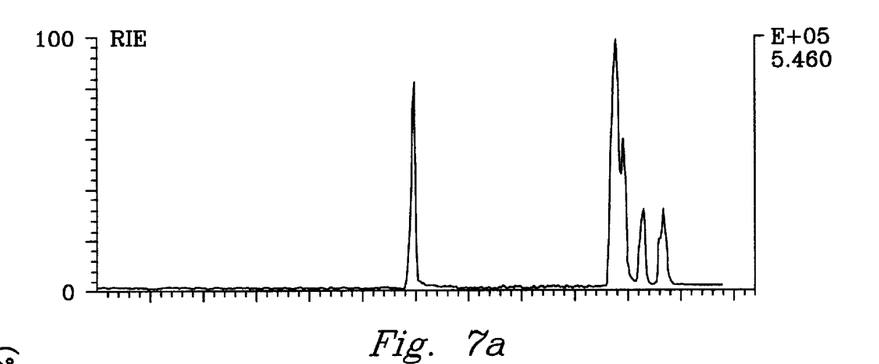
FIG. 7a is a mass electropherogram of a separation of benzenesulphonamides with a first interface made according to the present invention.
Figure 7B:
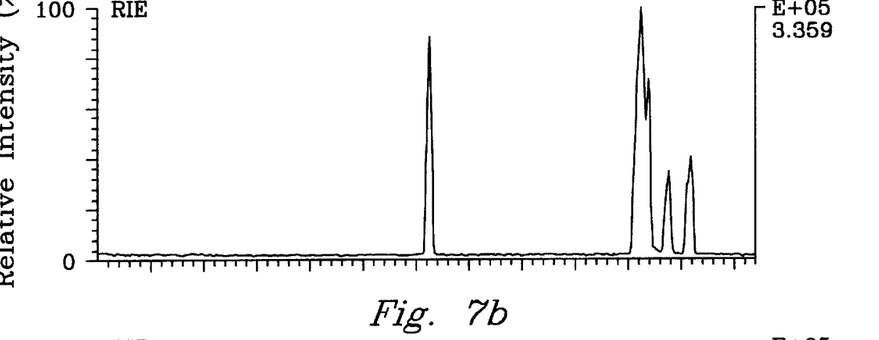
FIG. 7b is a mass electropherogram of a separation of benzenesulphonamides with a second interface made according to the present invention.
Figure 7C:
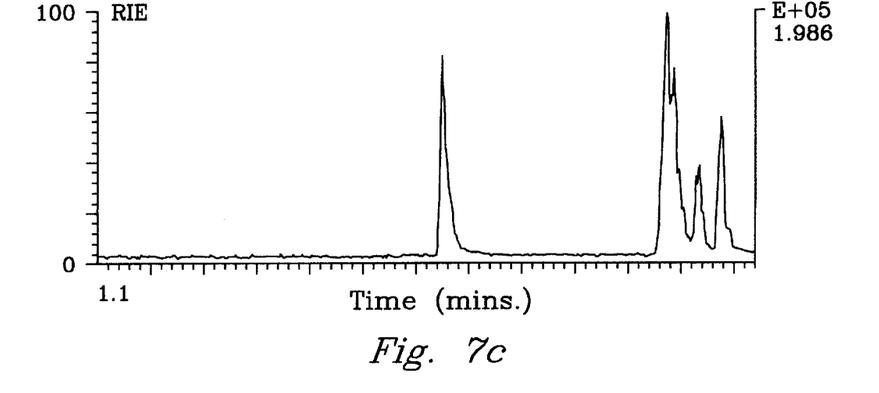
FIG. 7c is a mass electropherogram of a separation of benzenesulphonamides with a third interface made according to the present invention.

A difference in migration times is always noted between UV, sheath-flow ESI-MS and micro-dialysis junction ESI-MS detection due to the differences in electric fields and boundary effects. However, a relatively large variation in migration times through different CE capillaries is also common if they are not fully conditioned. FIGS. 7a, 7b and 7c illustrate the reproducibility obtained from three separately constructed interfaces (i.e. three different capillaries and tips). The three interfaces were essentially identical according to the present invention. For this, no time was expended in optimizing relative capillary positions and flow-rates, but relatively good reproducibility (within CE-MS standards) was still achieved. However, the third separation has a lower separation efficiency, an observation attributed to poor capillary cuts at the junction.

Table 1 shows average percentage coefficients of variation in migration time, peak area and peak efficiency for the first, fourth, and fifth peaks for 3 runs obtained using a single capillary and for 3 runs obtained with 3 different capillaries. These results were achieved despite little time being spent in capillary conditioning; also results were calculated from only a small number of runs and no internal standard was applied.

TABLE 1

Comparison of coefficients of variation (c. of v.) in migration times, efficiency and peak areas calculated from 3 runs using (A) a single capillary and 3 runs using (B) 3 different capillaries.

|   | Migration Time (% c. of v.) | Efficiency (% c. of v.) | Peak Area (% c. of v.) |
|---|---|---|---|
| A | 3.1 | 13 | 20 |
| B | 3.6 | 38 | 37 |

Figures 8A, 8B:
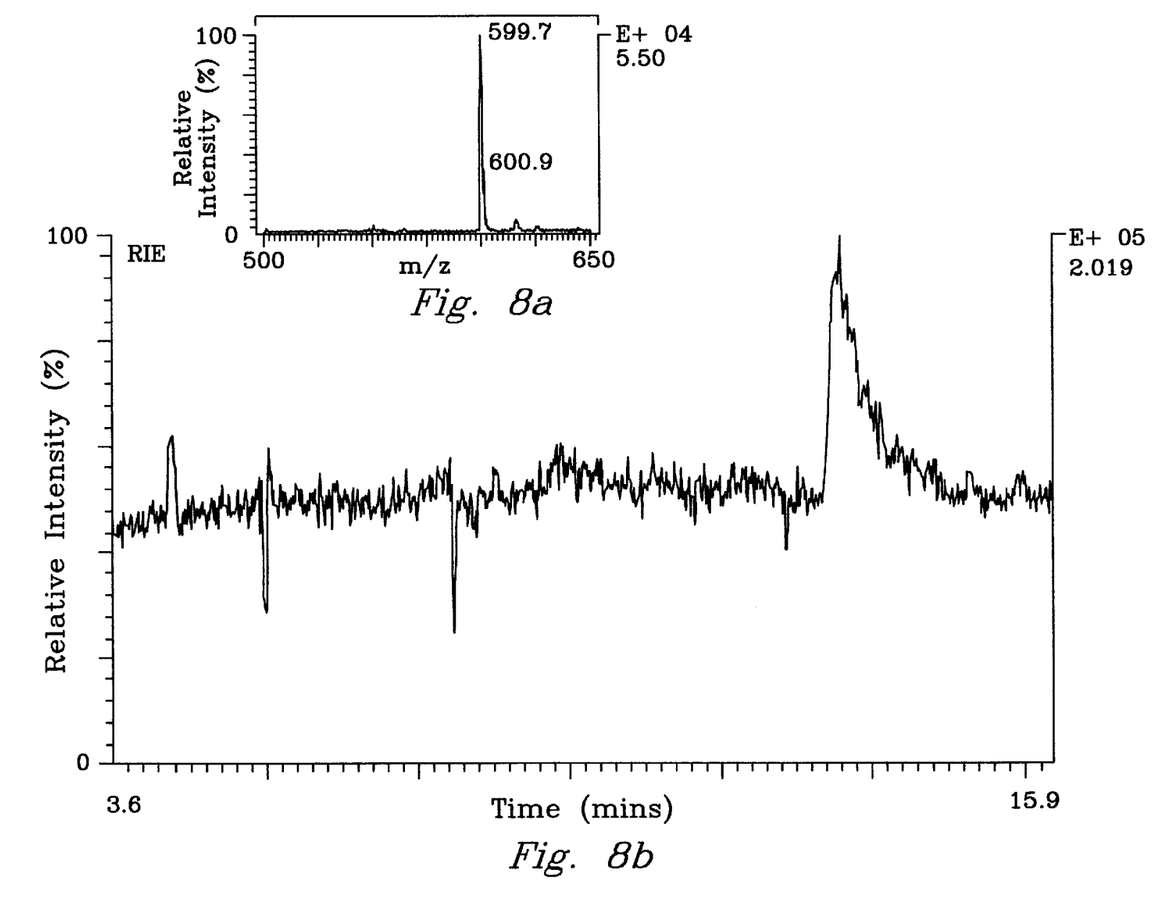
FIG. 8a is a mass spectrum of FMAF with separation conditions using polyacrylamide coated capillary and 10 mM $NH_4OAc$ (pH 7.9), 30 kV.
FIG. 8b is a mass electropherogram of FMAF with separation conditions using polyacrylamide coated capillary and 10 mM $NH_4OAc$ (pH 7.9), 30 kV.

FIGS. 8a and 8b show the mass spectrum (FIG. 8a) and mass electropherogram (FIG. 8b) of the peptide FMAF (MW=598) obtained using a polyacrylamide coated capillary. The polyacrylamide neutralizes the negative charge on the silica capillary walls and therefore minimizes the EOF. CE-MS under these very low flow-rate conditions employing a sheathless interface would not have been feasible. The stability of the polyacrylamide coating is known to be limited, especially under extremes of pH. However, the polyacrylamide was active during this particular run as over the coarse of the following few analyses, evidenced by a steady rise in the electrospray current and the background signal was observed as the coating degenerated and EOF increased.

Example 4

An experiment was conducted to demonstrate a further advantage of the interface 100 (micro-dialysis junction), specifically post-column solution changes, or the ease with which the composition of the electrolyte in the junction reservoir can be changed to manipulate the separation, the ESI process or the anolyte. This can be useful for capillary isoelectric focusing and capillary isotachophoresis as well as post-run acidification to aid the ESI process or to study non-covalent interactions. We have previously demonstrated that it is possible to shift the charge-state distribution of a protein by this technique, however, it was not clear that solution conditions could be altered sufficiently to disrupt a noncovalent complex in this on-line manner.

Figure 9A:
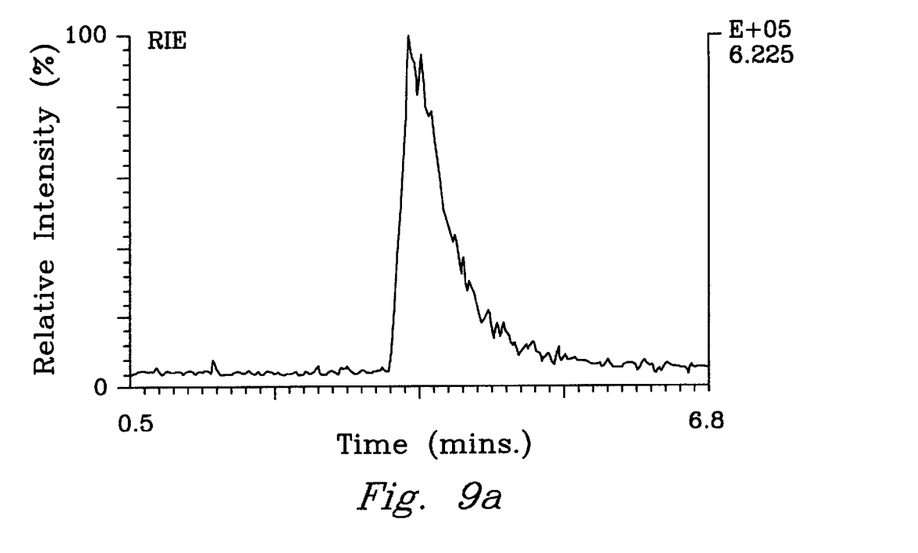
FIG. 9a is a mass electropherogram of horse-skeletal muscle myoglobin with a separation electrolyte=junction electrolyte=10 mM, pH 7.9, $NH_4OAc$.
Figure 9B:
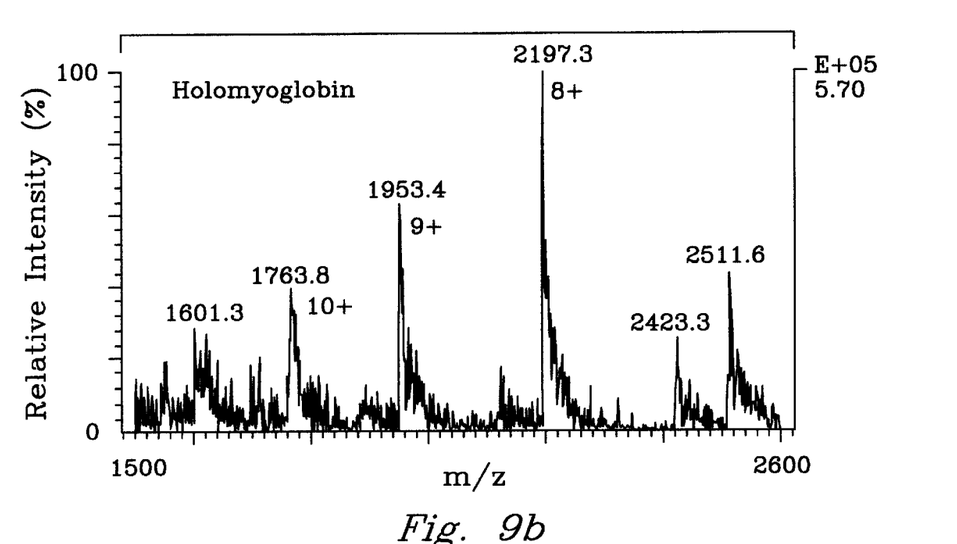
FIG. 9b is a mass spectrum of horse-skeletal muscle myoglobin with a separation electrolyte=junction electrolyte=10 mM, pH 7.9, $NH_4OAc$.

FIGS. 9a and 9b show the mass electropherogram (FIG. 9a) and mass spectrum (FIG. 9b) obtained for horse-skeletal-muscle myoglobin when the electrolyte in the CE capillary and in the reservoir was composed of 10 mM ammonium acetate (pH 7.9). The anolyte peak is relatively broad under these non-optimized separation conditions. The intact holomyoglobin complex was maintained throughout the separation and 'soft' ESI process.

Figure 10A:
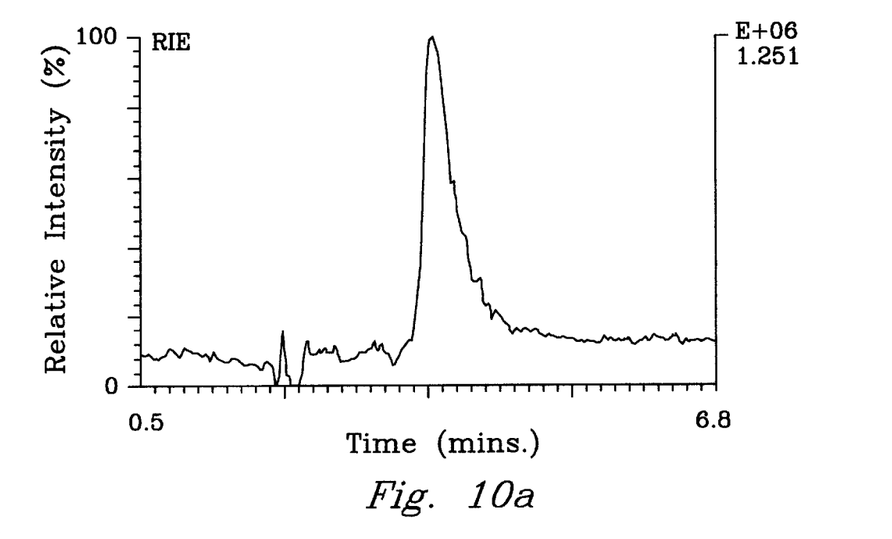
FIG. 10a is a mass electropherogram of horse-skeletal muscle myoglobin with a separation electrolyte=10 mM, pH 7.9, $NH_4OAc$, and a junction electrolyte=1% HOAc.
Figure 10B:
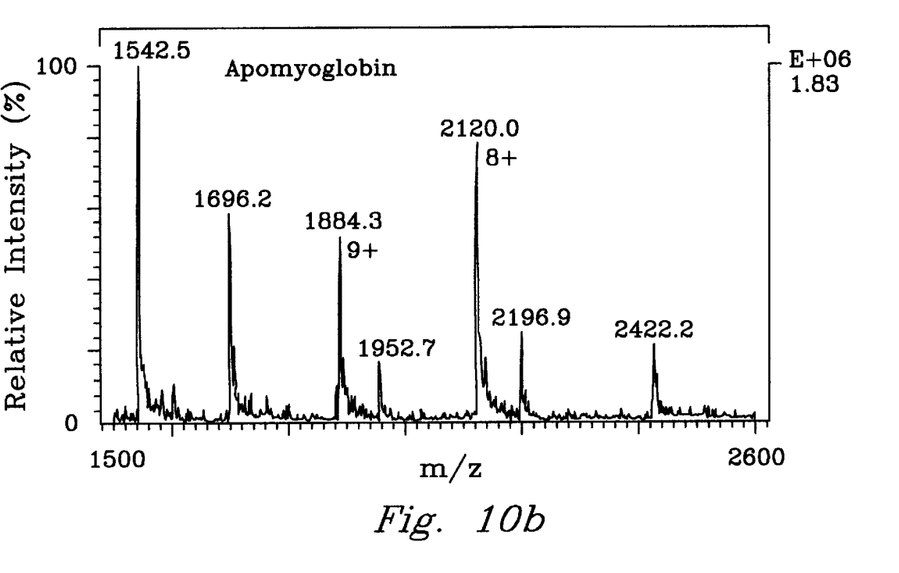
FIG. 10b is a mass spectrum of horse-skeletal muscle myoglobin with a separation electrolyte=10 mM, pH 7.9, $NH_4OAc$, and a junction electrolyte=1% HOAc.

FIGS. 10a and 10b show the mass electropherogram (FIG. 10a) and mass spectrum (FIG. 10b) obtained when the electrolyte in the reservoir was changed to 1% acetic acid. In this case the myoglobin migrated through the capillary as the intact complex, but on traversing the junction was denatured, is denatured and loses the heme moiety. The mass spectrum using the acidic junction conditions is clearly more intense and shows a predominance of ions due to the denatured protein.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An interface between a capillary electrophoresis separation capillary end and an electrospray ionization mass spectrometry emitter capillary end with a gap therebetween, for transporting an anolyte sample from a capillary electrophoresis separation capillary to a electrospray ionization mass spectrometry emitter capillary, the interface having:

(a) a reservoir containing an electrolyte surrounding both of said capillary electrophoresis capillary end and said electrospray ionization mass spectrometry emitter capillary end; and (b) an electrode immersed into said electrolyte, said electrode closing a capillary electrophoresis circuit and providing charge transfer whereby a voltage is supplied for electrospraying; wherein the improvement comprises:

a charge transfer fitting having a first end enclosing said charge capillary electrophoresis capillary end, said charge transfer fitting extending therefrom across said gap and having a second end enclosing said electrospray ionization mass spectrometry emitter capillary end, said charge transfer fitting permitting said charge transfer from said electrode through said electrolyte across said charge transfer fitting into said anolyte sample and avoiding substantial bulk fluid transfer across said charge transfer fitting.

2. The interface as recited in claim 1, wherein said electrolyte is substantially electrochemically similar to said anolyte sample thereby avoiding substantial ion transfer or bulk fluid transfer across the charge transfer fitting.

3. The interface as recited in claim 1, wherein said charge transfer fitting is a microdialysis tube.

4. The interface as recited in claim 1, wherein said electrospray ionization mass spectrometry emitter capillary is less than or equal to about 2 cm in length.

5. A method of providing an interface between a capillary electrophoresis separation capillary end and an electrospray ionization mass spectrometry emitter capillary end with a gap therebetween, for transporting an anolyte sample from a capillary electrophoresis separation capillary to a electrospray ionization mass spectrometry emitter capillary, the method having the steps of:

(a) surrounding both of said capillary electrophoresis capillary end and said electrospray ionization mass spectrometry emitter capillary end with an electrolyte; and (b) immersing an electrode into said electrolyte, and closing a capillary electrophoresis circuit thereby providing charge transfer whereby a voltage is supplied for electrospraying; wherein the improvement comprises:

placing a charge transfer fitting having a first end enclosing said charge capillary electrophoresis capillary end, said charge transfer fitting extending therefrom across said gap and having a second end enclosing said electrospray ionization mass spectrometry emitter capillary end, said charge transfer fitting permitting said charge transfer from said electrode through said electrolyte across said charge transfer fitting into said anolyte sample and avoiding substantial bulk fluid transfer across said charge transfer fitting.

6. The method as recited in claim 5, wherein said electrolyte is substantially electrochemically similar to said anolyte sample thereby avoiding substantial ion transfer or bulk fluid transfer across the charge transfer fitting.

7. The method as recited in claim 5, wherein said charge transfer fitting is a microdialysis tube.

8. The method as recited in claim 5, wherein said electrospray ionization mass spectrometry emitter capillary is about 2 cm in length.

9. A junction interface between a capillary electrophoresis separation capillary end and an electrospray ionization mass spectrometry emitter capillary end with a gap therebetween, for transporting an anolyte sample from a capillary electrophoresis separation capillary to a electrospray ionization mass spectrometry emitter capillary, the interface having:

(a) a reservoir containing an electrolyte surrounding both the capillary electrophoresis separation capillary end and the electrospray ionization mass spectrometry emitter capillary end; and (b) an electrode immersed into said electrolyte, said electrode closing a capillary electrophoresis circuit and providing charge transfer from said electrolyte through said gap into said anolyte sample, whereby a voltage is supplied for electrospraying;

wherein the improvement comprises:

a microdialysis tube having a first end enclosing the capillary electrophoresis separation capillary end, extending across said gap and enclosing the electrospray ionization mass spectrometry emitter capillary end.

* * * * *

UNITED STATES PATENT AND TRADEMARK OFFICE
CERTIFICATE OF CORRECTION

PATENT NO.   : 5,993,633
DATED        : November 30, 1999
INVENTOR(S)  : Smith et al.

It is certified that error appears in the above-identified patent and that said Letters Patent is hereby corrected as shown below:

Column 6,
Line 24, please remove the coma after "A".

Signed and Sealed this

Eighteenth Day of February, 2003

JAMES E. ROGAN
*Director of the United States Patent and Trademark Office*